United States Patent
Hoshino et al.

(10) Patent No.: US 6,664,082 B1
(45) Date of Patent: Dec. 16, 2003

(54) GENETICALLY ENGINEERED L-SORBOSE REDUCTASE-DEFICIENT MUTANTS

(75) Inventors: Tatsuo Hoshino, Kamakura (JP); Takahide Kon, Yokohama (JP); Masako Shinjoh, Kamakura (JP); Masaaki Tazoe, Yokohama (JP)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/266,320

(22) Filed: Mar. 11, 1999

(30) Foreign Application Priority Data

Mar. 13, 1998 (EP) .............................................. 98104546

(51) Int. Cl.$^7$ ............................ C12P 19/02; C12N 9/04; C12N 1/21; C12N 15/52; C12N 15/87
(52) U.S. Cl. .................... 435/105; 435/190; 435/252.3; 435/463; 435/471; 435/473
(58) Field of Search ................................. 435/463, 471, 435/473, 190, 252.3, 105

(56) References Cited

FOREIGN PATENT DOCUMENTS

| EP | 0 233 050 A2 | 8/1987 |
|---|---|---|
| EP | 0 728 840 A2 | 8/1996 |

OTHER PUBLICATIONS

Sugisawa, Teruhide et al., *Purification and Properties of NADPH–Linked L–sorbose Reductase from Gluconobacter melanogenus N44–1*, Agri. Biol. Chem., vol. 55 (8), pp. 2043–2049 (1991).

*Primary Examiner*—Elizabeth Slobodyansky
(74) *Attorney, Agent, or Firm*—Bryan Cave LLP

(57) ABSTRACT

The present invention provides a genetically engineered microorganism belonging to the genus Gluconobacter or Acetobacter, which has an engineered gene for the biological activity of reducing L-sorbose which is more than 90% non-functional in developing the said biological activity. The engineered microorganism is derived from a microorganism belonging to the genus Gluconobacter or Acetobacter, and has the biological activity for reducing L-sorbose that is less than 10% of the amount of the activity of the wild type organism. The present invention further provides a method for producing the genetically engineered microorganism by mutating the gene of a microorganism of the genus Gluconobacter or Acetobacter which encodes a protein having the L-sorbose reductase activity, determining the L-sorbose reductase activity of the resulting microorganism with the mutated gene and selecting the genetically engineered microorganism having L-sorbose reductase activity that is less than 10% of the amount of the activity of the wild type microorganism.

11 Claims, 7 Drawing Sheets

```
              Met Thr Ile Thr Glu Gly Gly Tyr        SEQ ID NO:3
           5'                                 3'
PRIMER 1      ATG ACC ATC ACC GAA GGA GGA TA         23mer, 144 MIXTURE
               G   T   G   G   C   C
                               T   T
```

```
              Phe Pro Asn Gly Met Val Asp Arg        SEQ ID NO:4
           5'                                 3'
              TTC CCC AAC GGA ATG GTC GAC CG
                G   T   C       G   T
                T       T   T
```

```
           5'                                 3'
PRIMER 3R     CG ATC AAC CAT ACC ATT AGG GAA         23mer, 108 MIXTURE
                  G   C       G   G   G
                      G           T   C
```

GENETICALLY ENGINEERED L-SORBOSE REDUCTASE-DEFICIENT MUTANTS

FIELD OF THE INVENTION

The present invention relates to genetically engineered L-sorbose reductase-deficient mutants of a microorganism belonging to the genus Gluconobacter or Acetobacter. The present invention also relates to the production of L-sorbose by fermentation as well as to the production of vitamin C.

BACKGROUND OF THE INVENTION

The production of vitamin C has been conducted by Reichstein method which involves a fermentation process for the conversion from D-sorbitol to L-sorbose by a microorganism belonging to the genus Gluconobacter or Acetobacter, as a sole biological step. The said conversion to L-sorbose is one of the key steps for the efficiency of vitamin C production. It was, however, observed that the product, L-sorbose, was consumed after the consumption of the substrate, D-sorbitol, during the oxidative fermentation with the said microorganism. This phenomenon was understood that L-sorbose was reduced by NADPH-linked L-sorbose reductase (hereinafter occasionally referred to as SR) present in the cytosol (See: Sugisawa et al., Agric. Biol. Chem. 55: 2043–2049, 1991). It was reported that, in Gluconobacter, D-sorbitol was converted to D-fructose which could be incorporated into the pentose pathway and further metabolized to $CO_2$ (Shinjoh et al., Agric. Biol. Chem. 54: 2257–2263, 1990). Such pathways consuming the product as well as the substrate might have caused less productivity of vitamin C ultimately.

An improvement of L-sorbose production was reported by Nogami et al. in Japanese Patent Application Kokai No. 51054/1995. They subjected the microorganisms of *Gluconobacter oxydans* and *Gluconobacter suboxydans* to conventional chemical mutagenesis and isolated the mutant strains whose ability of utilizing D-sorbitol as a sole assimilable carbon source was reduced. By applying such mutant to the fermentation for L-sorbose production, they observed more than 2~3% improvement of the productivity in comparison with the productivity of the parent strain.

One of the disadvantages which is often observed in mutant strains produced by the conventional mutagenesis is back mutation which nullifies the improved characteristics of the mutant strains during the course of fermentation or subculture of the mutant, which would result in decreased productivity of vitamin C ultimately. Therefore a stably mutated strain with respect to L-sorbose reductase is desired.

SUMMARY OF THE INVENTION

The present invention provides a genetically engineered microorganism belonging to the genus Gluconobacter or Acetobacter, which has an engineered gene for the biological activity of reducing L-sorbose which is more than 90% non-functional in developing the said biological acitivity. The engineered microorganism is derived from a microorganism belonging to the genus Gluconobacter or Acetobacter, and has the biological activity for reducing L-sorbose that is less than 10% of the amount of the activity of the wild type organism.

The present invention also provides a method for producing L-sorbose by incubating the genetically engineered microorganism in a medium, and obtaining L-sorbose from the medium. L-Sorbose produced in this manner can be used in the manufacture of vitamin C.

The present invention further provides a method for producing the genetically engineered microorganism by mutating the gene of a microorganism of the genus Gluconobacter or Acetobacter which encodes a protein having the L-sorbose reductase activity, determining the L-sorbose reductase activity of the resulting microorganism which has the mutated gene and selecting the genetically engineered microorganism having L-sorbose reductase activity that is less than 10% of the amount of the activity of the wild type microorganism.

BRIEF DESCRIPTION OF THE FIGURES

FIG. 2 illustrates oligonucleotide primers used for PCR cloning of SR gene from *G. suboxydans* IFO 3291. The primers shown are Primer 1. (SEQ ID NO: 7), which was synthesized in accordance with the amino acid sequence of SEQ ID NO: 3, a second primer (SEQ ID NO: 8) which was synthesized in. accordance with the amino acid sequence of SEQ ID NO: 4, and Primer 3R (SEQ ID NO: 9).

DETAILED DESCRIPTION OF THE INVENTION

Figure 1:
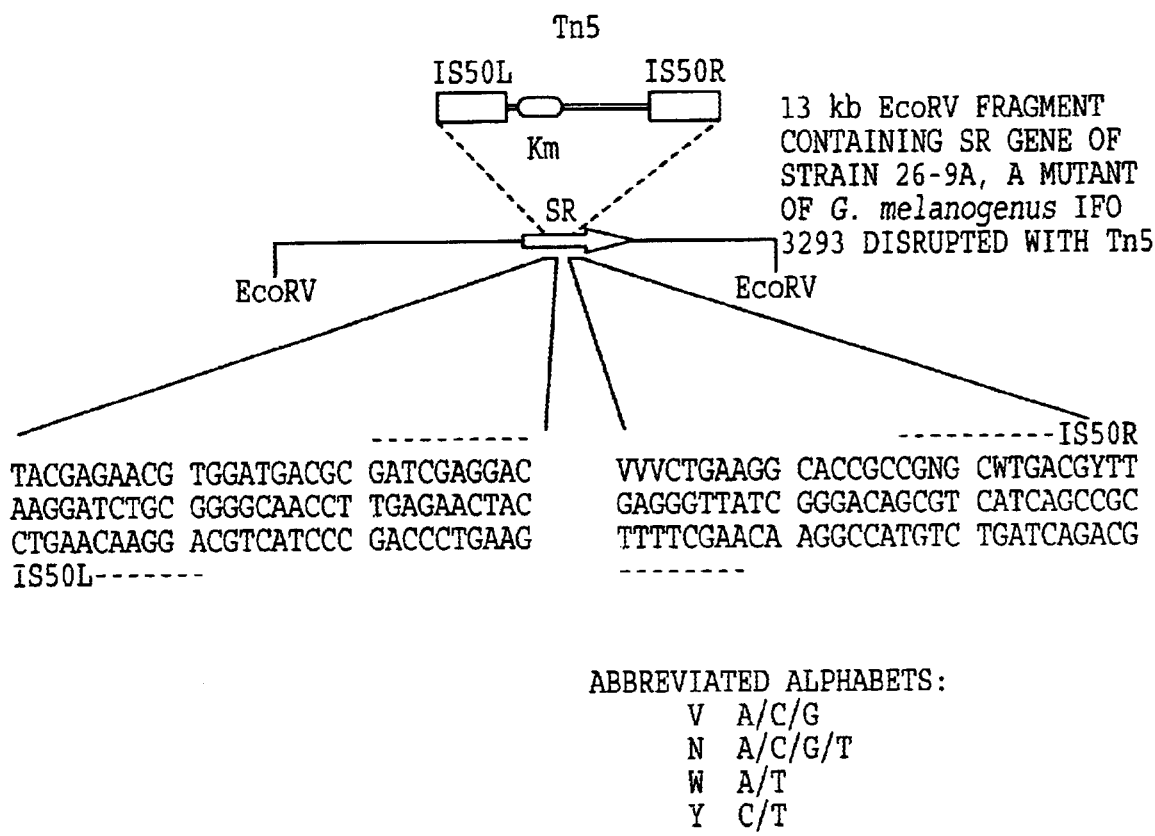
FIG. 1 illustrates the nucleotide sequences upstream (SEQ ID NO: 5) and downstream (SEQ ID NO: 6) of the Tn5-inserted region of the chromosomal DNA of an L-sorbose reductase-deficient mutant, 26–9A derived from *G. melanogenus* IFO 3293.

In one aspect, the present invention provides a novel genetically engineered microorganism derived from a microorganism belonging to the genus Gluconobacter or Acetobacter which is characterized in that the biological activity thereof for reducing L-sorbose is substantially nullified by means of genetic engineering. And preferably it has the said biological activity less than 10% of that of the wild type microorganism; the said activity is 0.02 to 0.07 units/mg protein or less according to the definition of the activity described below (e.g. in Example 1 (iii)). The gene of the genetically engineered microorganism of the present invention may carry at least one mutation with the aid of disruption, addition, insertion, deletion and/or substitution of nucleotide(s) within the region required for the formation of active L-sorbose reductase in cells of the microorganism.

In one preferable embodiment of the genetically engineered microorganism of the present invention, the said mutation may be caused by the gene disruption within the region required for the formation of active L-sorbose reductase. Such disruption may contain at least one interfering DNA fragment selected from the group consisting of a transposon, an antibiotics resistant gene cassette and any DNA sequences which prevent the host microorganism from the formation of active L-sorbose reductase.

In another embodiment of the present invention, the said mutation may be produced by mutagenesis with the aid of site-directed mutagenesis. Such mutagenesis can be effected in the region required for the formation of active L-sorbose reductase, which region may include a structural gene of L-sorbose reductase or an expression control sequence such as a promoter, operator, terminator, DNA encoding repressor, activator and the like.

Another aspect of the present invention provides the use of an L-sorbose reductase gene of a microorganism belonging to the genus Gluconobacter or Acetobacter in producing the genetically engineered microorganism as described above, in which the said gene is characterized in that it encodes the amino acid sequence of L-sorbose reductase described in SEQ ID NO: 2 or its functional equivalents containing insertion, deletion, addition and/or substitution of one or more amino acid(s) in said SEQ ID NO: 2.

A further aspect of the present invention provides an efficient method for producing L-sorbose by the fermentation of a microorganism in an appropriate medium, which comprises use of the genetically engineered microorganism of the present invention described above. In connection to this L-sorbose production method, the present invention also provides an efficient vitamin C production process containing a fermentation step for the production of L-sorbose which is characterized in that the said fermentation is carried out by using the genetically engineered microorganism of the present invention as described above.

The present invention provides a novel genetically engineered microorganism derived from a microorganism belonging to the genus Gluconobacter or Acetobacter which is characterized in that the biological activity thereof for reducing L-sorbose is substantially nullified by means of genetic engineering.

The said genetically engineered microorganism may be a microorganism belonging to genus Gluconobacter or Acetobacter, which includes *Gluconobacter albidus, Gluconobacter capsulatus, Gluconobacter cerinus, Gluconobacter dioxyacetonicus, Gluconobacter gluconicus, Gluconobacter industrius, Gluconobacter melanogenus* (IFO 3293 and FERM P-8386 [National Institute of Bioscience and Human-Technology, Japan]), *Gluconobacter nonoxygluconicus, Gluconobacter oxydans, Gluconobacter oxydans subsp. sphaericus Gluconobacter roseus, Gluconobacter rubiginosus, Gluconobacter suboxydans* (IFO 3291), *Acetobacter xylinum* [commercially available from the Institute of Fermentation, Osaka, Japan (IFO) as IFO 3288], *Acetobacter pasteurianus, Acetobacter aceti, Acetobacter hansenii* and *Acetobacter liquefaciens* (IFO 12388; ATCC 14835). For strain information see also European Patent Application Publ. No. (EPA) 213591 and 518136. *Gluconobacter suboxydans* IFO 3291 has been deposited in the form of a mixture with *Gluconobacter oxydans* DSM4025 as FERM BP-3813 and *Gluconobacter melanogenus* IFO 3293 as FERM BP-8256. Further details can be taken from EP 518136. For *Gluconobacter suboxydans* (IFO 3291) and *Gluconobacter melanogenus* (IFO 3293), see also U.S. Pat. No. 5,747,301.

For the purpose of nullifying the biological activity of the said microorganism in reducing L-sorbose, the present invention involves genetic engineering to target the region of the gene of the microorganism required for the formation of the active L-sorbose reductase. The typical methodologies for this purpose are known, such as gene disruption with transposon or selection marker gene cassette and site-directed mutagenesis. As it is described below, gene disruption method is useful to identify the target gene of the microorganism as well as to block the gene function. Once the above mentioned target region of the gene has been identified, conventional mutagenesis can also be applicable by the treatment of the target DNA fragment with e.g. a chemical mutagen, ultra violet irradiation and the like.

Gene disruption may be carried out by the introduction of an interfering DNA fragment into chromosomal DNA of the microorganism with the aid of transposon mutagenesis, introduction of a gene cassette carrying a selection marker such as an antibiotics resistant gene, or site-directed mutagenesis. The introduced DNA sequences substantially nullify the formation of active L-sorbose reductase.

(a) Transposon Mutagenesis:

Transposon mutagenesis is known as a potent tool for genetic analysis (P. Gerhardt et al., "Methods for General and Molecular Bacteriology" Chapter 17, Transposon Mutagenesis; American Society for Microbiology, 1994). This method utilizes a transposable elements which are distinct DNA segments having the unique capacity to move (transpose) to new sites within the genome of the host organisms. The transposition process is independent of the classical homologous recombination system of the organism. The insertion of a transposable element into a new genomic site does not require extensive DNA homology between the ends of the element and its target site. Transposable elements have been found in a wide variety of prokaryotic and eukaryotic organisms, where they can cause null mutations, chromosome rearrangements, and novel patterns of gene expression on insertion in the coding region or regulatory sequences of resident genes and operons.

Prokaryotic transposable elements can be roughly divided into three different classes. Class I consists of simple elements such as insertion sequences (IS elements), which are approximately 800 to 1,500 bp in length. IS elements normally consist of a gene which encodes an enzyme required for transposition (i.e. transposase), flanked by terminally repeated DNA sequences which serve as substrate for the transposase. IS elements were initially identified in the lactose and galactose utilization operons of enteric bacteria, where the elements were found to cause often unstable, polar mutation on insertion.

Class II consists of composite transposable elements. The members of this class are also referred to as transposons or Tn elements. Transposons in prokaryotes have been identified as a class of complex transposable elements, often containing simple IS elements (or parts thereof) as direct or inverted repeats at their termini, behaving formally like IS elements but carrying additional genes unrelated to transposition functions, such as antibiotic resistance, heavy-metal resistance or pathogenicity determinant genes. The insertion of a transposon into a particular genetic locus or replicon (phage) is designated by using a double colon, e.g. lacZ::Tn5 or λ::Tn5.

Class III includes "transposable" bacteriophages, such as Mu and its relatives. Phage Mu is both a virus and a transposon. It is known that it can integrate at multiple sites in the host chromosome, thereby frequently causing mutations.

Transposon mutagenesis utilizing the above transposable elements is known to result in the following:

(1) Such a mutation generally leads to inactivation of the gene, and the resulting null mutation is relatively stable.

(2) Transposons introduce new genetic and physical markers into the target locus, such as antibiotic resistance genes, new restriction endonuclease cleavage sites, and unique DNA sequences which can be identified by genetic means, e.g., DNA-DNA hybridization or electron microscopic heteroduplex analysis. The genetic markers are useful for mapping the mutated loci as well as screening the mutants.

(3) Transposons can generate a variety of genomic rearrangements, such as deletions, inversions, translocations, or duplications, and can be used to introduce specific genes into the target bacteria.

A variety of transposons are known in the art, such as Tn3, Tn5, Tn7, Tn9, Tn10, phage Mu and the like. Among them, Tn5 is known to have almost no insertion specificity, and its size is relatively small. Tn5 is also one of the most frequently used transposable elements which is readily derived from the sources, such as pfd-Tn5 [American Type Culture Collection, USA (ATCC) ATCC 77330] or pCHR81 (ATCC 37535). For the purpose of use in the random mutagenesis in the practice of the present invention, Tn5 is preferred. A variety of Tn5 derivatives designated Mini-Tn5s, which consist of 19 bp of the Tn5 inverted repeats required for transposition coupled to antibiotic resistance or other selectable marker genes are also useful for the present invention. Such Mini-Tn5s are inserted into a suicide vector, in addition to the Tn5 transposase (tnp), to construct an efficient suicide Tn5 mutagenesis system. Further information regarding how to work with Tn5 transposons can be taken from the following references: P. Gerhardt et al., Chapter 17 cited above; K. N. Timmis et al., Mini-Tn5 Transposon Derivatives for Insertion Mutagenesis, Promoter Probing, and Chromosomal Insertion of Cloned DNA in Gram-Negative Eubacteria, J. Bacteriology, 172:6568–6572, 1990.

Information describing how Tn5 can be derived from pfd-Tn5 (see explanation of pfd-Tn5 (ATCC 77330)), is obtainable from the ATCC Home Page on the Internet. Accordingly, the suicide plasmid pfd-Tn5 can be introduced into E. coli as well as other Gram negative bacterium by electroporation (see the reference for recommended conditions). The plasmid itself can be used as a Tn5 donor. In addition, one can construct a suicide Tn5 vector by introducing pfd-Tn5 plasmid into the recipient E. coli with any plasmid which one wants to use, selecting transformants showing $Km^r$ and resistance of the target plasmid, isolating plasmids from the transformants, transforming E. coli with the isolated plasmids, and selecting for Km and plasmid-marker-resistant transformants to obtain E. coli strain carrying the target plasmid with Tn5. Concept of this protocol is also available in "Region-Directed Tn5 Mutagenesis" in P. Gerhardt et al. (cited above).

Random mutagenesis with transposon involves the introduction of a transposon into a target bacterial cell via transformation, transduction, conjugal mating or electroporation by using suicide plasmid or phage vectors. The resulting mutants may be screened with the aid of the marker carried by the transposon. Transposition of the transposon into the genome of the recipient bacterium can be detected after the vector used has been lost by segregation.

For the introduction of transposons into a microorganism of the genus Gluconobacter or Acetobacter, so-called suicide vectors including a derivative of phage P1 and narrow-host-range plasmids are commonly used. The phage P1 vectors and the plasmid vectors can be transferred by infection and by transformation, conjugal mating or electroporation, respectively, into the recipient cells, wherein these vectors preferably lack the appropriate origins of recipients. The choice of suicide vector and transposon to be used depends on criteria including phage sensitivity, intrinsic antibiotic resistance of the recipient cell and the availability of a gene transfer system such as transformation, conjugal transfer, electroporation, or infection to introduce transposon-carrying vector into E. coli.

One of the preferable vectors for use in the present invention is phage P1 (ATCC25404) which injects its DNA into a microorganism belonging to the genus Gluconobacter or Acetobacter, however, this DNA will be unable to replicate and will be lost by segregation. Such P1 phage carrying Tn5 (P1::Tn5) can be used in the form of phage lysate which may be prepared by lysing E. coli carrying P1::Tn5 in accordance with known procedures (see e.g., P. Gerhardt et al., Chapter 17, cited above, or U.S. Pat. No. 5,082,785, which is incorporated by reference herein).

The other preferable suicide vectors which can be used in the present invention are plasmid suicide vectors, which may be based on replicon derived from plasmid RP4, or its relative RK2 (ATCC37125), carrying the same broad-host-range conjugal transfer of mobilization functions and sites but a narrow-host-range origin of replication. These vectors can be mobilized at a high frequency from E. coli to a microorganism belonging to the genus Gluconobacter or Acetobacter but cannot be stably maintained in the recipient cells. These vectors contain, in addition to Tn5, the IncP-type mobilization (mob; oriT) site and are based on commonly used E. coli cloning vectors, such as pACYC177 (ATCC37031), pACYC184 (ATCC37033), and pBR325 [Bolivar F., 1978, Gene 4: 121–136; a derivative of pBR322 (ATCC31344)], all of which cannot replicate in nonenteric bacteria (pSUPseries, Simon R. et al., 1983, Bio/Technology 1: 784–791). pSUP-type plasmids can be mobilized in bi-parental mating experiments by providing the transfer function in trans from a chromosomally integrated copy of the IncP plasmid RP4 in the donor strain itself (e. g., strain S17-1) or in tri-parental mating experiments by providing the transfer functions from plasmid pRK2013 (ATCC37159) harbored by a nondonor, nonrecipient helper strain of E. coli.

The recipient cell which receives the transposon can be selected by the marker carried by the element, e.g. resistance to particular antibiotics. When Tn5 is used as a transposon, the marker of $Km^r$ or $Nm^r$ can be usually used. Besides $Km^r$ or $Nm^r$ markers, genetic markers of $Tc^r$, $Gm^r$, $Sp^r$, $Ap^r$, $Cm^r$ and the like can be used as the alternative marker genes. The other transposons carrying readily visualized gene products such as those encoded by lacZ, luxAB or phoA can also be used. These Tn5 derivatives are especially useful if the target bacterial strain has an intrinsic resistance to the antibiotics normally used to select for Tn5 (kanamycin, neomycin, bleomycin and streptomycin) or if a secondary mutagenesis of a strain already harboring a Tn5 derivative is to be carried out (P. Gerhardt et al., Chapter 17, cited above).

(b) Region-directed Mutagenesis

A powerful extension of the Tn5 mutagenesis protocol is the use of gene replacement techniques to substitute the wild-type gene in the original bacterial strain with its well-characterized Tn5-mutated analog carried by a plasmid in E. coli. When a wild-type locus has been cloned, region-directed mutagenesis with Tn5 or its derivatives or gene cassettes carrying selection markers can be used efficiently to inactivate the target genes and operons carried by the cloned region. For this purpose, Tn5 itself or its derivatives mentioned above or any gene cassettes with selection markers, e. g., $Km^r$ gene cassette carried by pUC4K (Pharmacia, Uppsala, Sweden) can be used. This approach is very efficient when one wants to inactivate the gene of interest, e. g., the gene of a mutant strain developed from the parent strain from which the wild-type gene was once cloned. The only limitation in these types of replacement experiments is the length of homologous sequences needed for the double-crossover recombination event; 0.5–5 kb long homologous sequences at both ends are preferably required.

The preferable vectors for the region-directed mutagenesis are the same as those useful for transposon mutagenesis, for example, the above mentioned suicide phage and plasmid vectors.

(c) Site-directed Mutagenesis

When a wild-type gene is cloned and its nucleotide sequence is determined, site-directed mutagenesis can also be used to inactivate the target genes. Oligonucleotide primers including addition and deletion of nucleotides for frame-shift, or substitution of nucleotides for introduction of stop codons or different codons are used for mutating genes of interest. The mutagenesis with the primers including mutation(s) can be conducted usually in *E. coli* with any commercial site-directed mutagenesis kit. This type mutagenesis is useful if Tn5- or region directed-cassette-mutagenesis causes polar effect affecting gene expression downstream or upstream.

The preferable vectors for introducing the mutated gene into the target microorganism are the same as those useful for transposon mutagenesis. In this case, aimed mutant can be isolated by biological assay, e.g., enzymological or immunological screening to detect deficiency of the target gene product. Alternatively, the mutated gene can be tagged with selection marker gene described above at the site not affecting gene expression downstream or upstream to facilitate the selection of the gene replacement. One can obtain the target gene disruptant more easily by combination of biological assay with marker-selection.

The L-sorbose reductase-deficient mutant can be selected generally as follows: 3,000 to 10,000 transposon mutants are subjected to the product assay with L-sorbose as the substrate to select the mutant which does not convert L-sorbose to D-sorbitol. The first screening can be done preferably in microtiter plates with the reaction mixture containing L-sorbose. The formation of the product, D-sorbitol, is first detected by TLC with appropriate developing solvent; candidates forming undetectable amount of D-sorbitol are selected.

Then, the candidate mutants are subjected to assay of L-sorbose reductase activity as exemplified in the Example 1 of the present invention to confirm L-sorbose reductase-deficiency.

For confirming that the deficient mutant really carries transposon, colony- or Southern-hybridization is usually conducted with labeled-DNA fragment containing the transposon used as the probe by the standard methods (Molecular cloning, a laboratory manual second edition, Maniatis T., et al., 1989).

Such a mutant was isolated as described in Example 1 of the present invention. The transposon mutant is useful for further identifying the target L-sorbose reductase gene and determining its nucleotide sequence of the region tagged with the transposon.

The DNA fragment inserted by a transposon can be cloned into any *E. coli* cloning vector, preferably pUC18, pUC19, pBluescript II (Stratagene Cloning Systems, CA, USA) or their relatives, by selecting transformants showing both phenotypes of selection markers of the vector and the transposon. The nucleotide sequences adjacent to the transposon are able to be determined by e. g., a chain termination method (Sanger F. S., et al., Proc. Natl. Acad. Sci. USA 74:5463–5467,1977). The resulting nucleotide sequences may be partial sequences whose reading frame might not be known at this time.

Once the nucleotide sequences are determined, they can be subjected to homology search performed with nucleotide and/or protein sequence data bases by using a genetic analysis program, e. g., BLASTP search (Lipman et al., J. Mol. Biol. 215: 403–410, 1990). If any homologous sequences are found, their amino acid sequences can be aligned to find any consensus sequences which are conserved between the homologous proteins. According to the consensus sequences, oligonucleotide primers can be synthesized and used to amplify the partial DNA of the target gene by polymerase chain reaction (PCR). Besides the consensus sequences, any amino acid sequences which are determined after adjusting the reading frame by the alignment of homologous proteins, can be used for designing the PCR primers.

The resulting PCR-bom partial gene can be used as a probe to obtain the whole target gene through Southern- and colony-hybridization. Southern-hybridization reveals size of the DNA fragment containing the target gene and one can construct a mini-gene library containing the DNA fragments with the aimed size. The mini-library can then be screened with the partial gene as the probe by colony-hybridization to obtain the whole target gene. Then the complete nucleotide sequence of the target gene can be determined to identify its open reading frame.

The region inserted by a transposon may be a regulatory gene controlling the expression of the structural gene of L-sorbose reductase; the regulatory gene can also be the target for disrupting the L-sorbose reductase gene.

Figure 4:
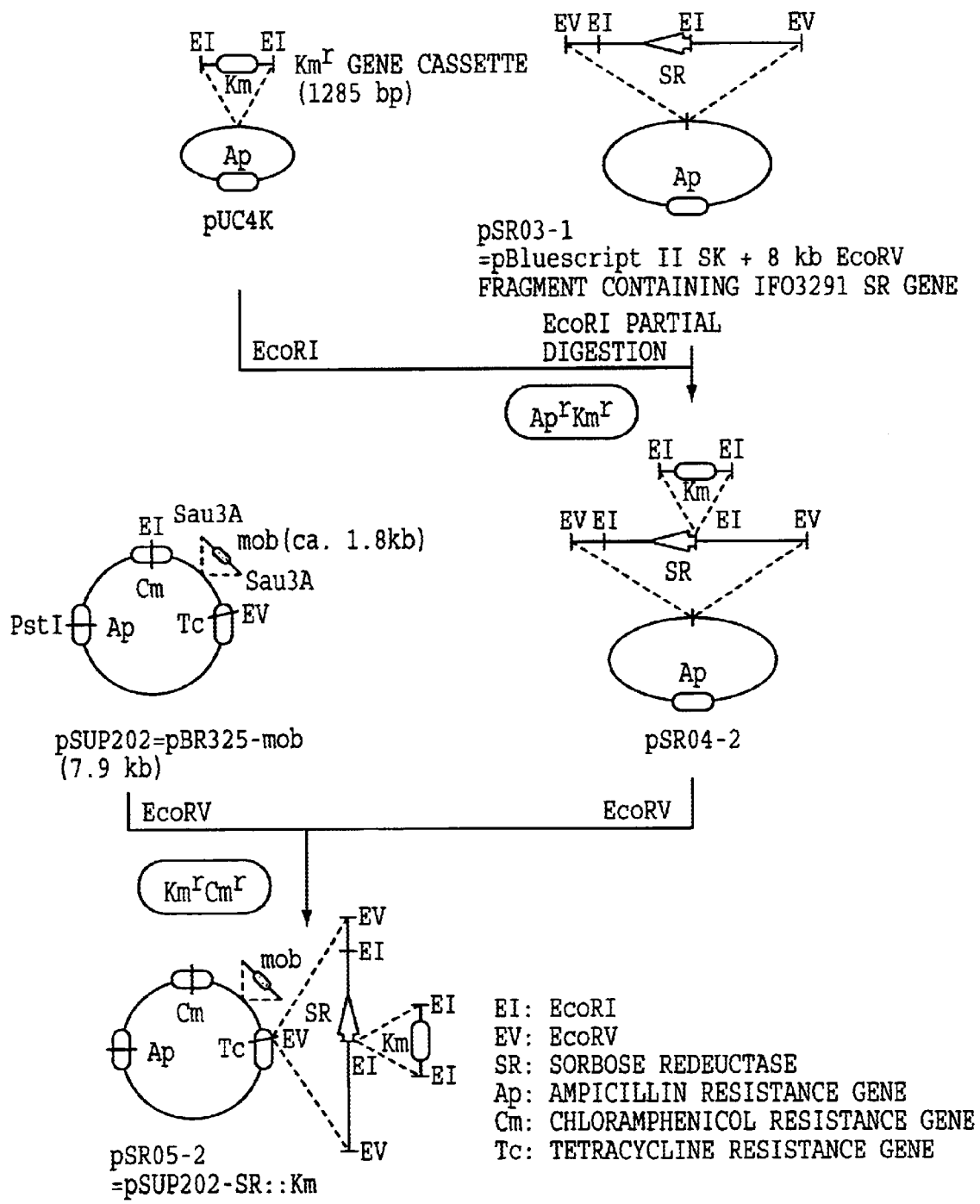
FIG. 4 is a scheme for the construction of a suicide plasmid for disruption of L-sorbose reductase gene in *G. suboxydans* IFO 3291.
Figure 5:
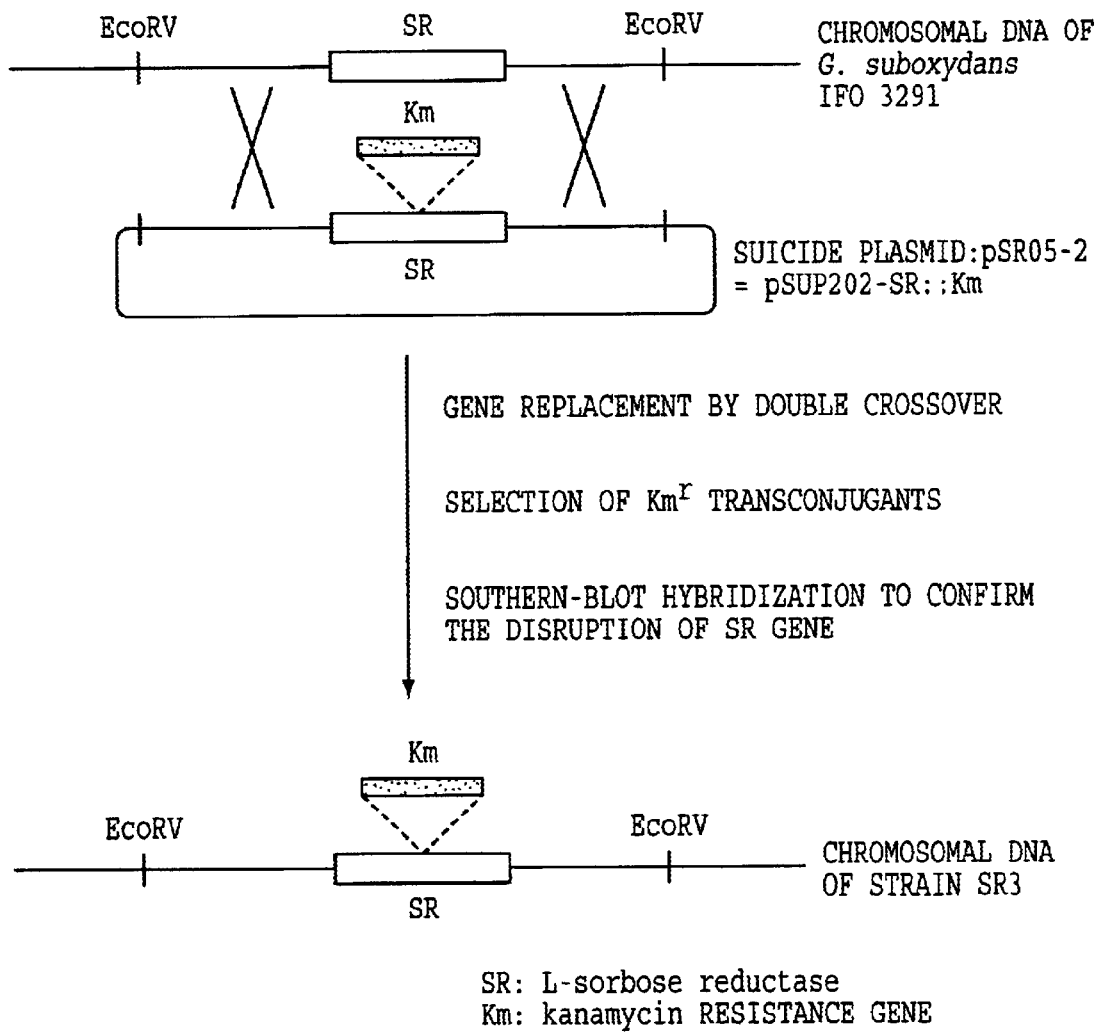
FIG. 5 illustrates a schematic mechanism for the disruption of L-sorbose reductase gene of *G. suboxydans* IFO 3291.

Cloned DNA fragment containing the partial or whole L-sorbose reductase gene of the target microorganism can be used for disrupting the L-sorbose reductase gene of the target microorganism. A schematic procedure and mechanism for the disruption are illustrated in FIGS. 4 and 5, respectively. The DNA fragment is first cloned into *E. coli* vector such as pBluescript II SK. Then a gene cassette carrying a selection marker such as $Km^r$ gene is inserted into the target L-sorbose reductase gene so that it will not form active L-sorbose reductase. The resulting DNA fragment with disrupted L-sorbose reductase gene is recloned on a suicide vector such as pSUP202. The suicide plasmid carrying disrupted gene can be introduced into the recipient microorganism by any gene transfer methods including conjugal mating as described above. Selection of the target mutant generated by double crossover recombination event can be done by isolating colonies expressing the selection marker gene (e.g., $Km^r$) and characterizing its chromosomal DNA by Southern-blot hybridization. The L-sorbose reductase deficiency of the candidate mutant is confirmed not to show detectable enzyme activity of L-sorbose reductase.

Such a mutant was isolated as described in Example 5 of the present invention as the strain SR3. Non-assimilation of L-sorbose can be examined with any media containing 1–500 g/L of D-sorbitol for L-sorbose fermentation by chasing the concentration of L-sorbose once converted from D-sorbitol in the fermentation broth. Instead, L-sorbose-containing medium can also be used for confirming non-assimilation of L-sorbose under fermentation conditions.

The mutants provided in the present invention may be cultured in an aqueous medium supplemented with appropriate nutrients under aerobic conditions. The cultivation may be conducted at pH between about 3.0 and 9.0, preferably between about 5.0 and 8.0. While the cultivation period varies depending upon pH, temperature and nutrient medium used, usually 1 to 6 days will bring about favorable results. A preferred temperature range for carrying out the cultivation is from about 13° C. to 45° C., preferably from about 18° C. to 42° C.

It is usually required that the culture medium contains such nutrients as assimilable carbon sources, digestible nitrogen sources and inorganic substances, vitamins, trace elements and the other growth promoting factors. As assimilable carbon sources, glycerol, D-glucose, D-mannitol, D-fructose, D-arabitol, D-sorbitol, L-sorbose, and the like can be used.

Various organic or inorganic substances may also be used as nitrogen sources, such as yeast extract, meat extract, peptone, casein, corn steep liquor, urea, amino acids, nitrates, arnmonium salts and the like. As inorganic substances, magnesium sulfate, potassium phosphate, ferrous and ferric chlorides, calcium carbonate and the like may be used.

The L-sorbose reductase-deficient mutant of the present invention can be applied to the fermentative oxidation of D-sorbitol and is expected to improve the yield of vitamin C by increasing L-sorbose usable for the step of condensation reaction of L-sorbose to produce diacetone-L-sorbose. As it is apparent for those skilled in the art, the L-sorbose reductase-deficient mutant of the present invention may be applied to any processes for vitamin C production which include L-sorbose as a reaction intermediate.

SEQ ID NO. 1 is a linear, double stranded, genomic polynucleotide having 1458 base pairs. Its source is *Gluconobacter suboxydans* IFO 3291.

SEQ ID NO. 2 is an amino acid sequence of 485 residues. Its source is *Gluconobacter suboxydans* IFO 3291, in that it sets forth the deduced amino acid sequence.

SEQ ID NOs. 3 and 4 are peptides, each having 8 residues. Their source is *Gluconobacter melanogenus* IFO 3293. For further information, see Example 3.

The present invention is further illustrated with Examples described below:

EXAMPLE 1

Isolation of L-sorbose Reductase-deficient Tn5 Mutant from *G. melanogenus* IFO 3293 Derivative (i) Tn5 Mutagenesis.

Transposon mutagenesis was carried out (Manning R. F. et al., U.S. Pat. No. 5,082,785) to construct L-sorbose reductase deficient strain from 2-keto-L-gulonic acid-producing L42-9 strain. Any strains which produce L-sorbose from D-sorbitol and assimilate the resulting L-sorbose by L-sorbose reductase of the present invention can be obtained from *G. melanogenus* IFO 3293 by means of multi-step mutations with chemical mutagens including NTG and ICR170, ultraviolet irradiation etc. *E. coli* W3110 carrying P1::Tn5 maintained on LB agar plate containing 30 μg/ml of kanamycin was inoculated into 5 ml of P1 medium (LB supplemented with 0.01 M MgSO$_4$7H$_2$O and 10 μg/ml thymine) and cultivated at 30° C. overnight. One ml of this culture was transferred to 100 ml of the same medium in a 500 ml-Erlenmyer flask and grown to OD550 of approximately 0.09 at 30° C. for 95 min. The resulting culture was cooled on ice for 10 min and centrifuged at 3500 rpm at 4° C. for 20 min. The cells were suspended in 25 ml of P1 medium and the cell suspension was transferred to a 300 ml-flask and incubated at 42° C. for 20 min without shaking. When lysis of the cell was observed by standing at 37° C. for 90 min, the cells were lysed by adding 0.5 ml of chloroform. The mixture was then vortexed thoroughly, stood at room temperature for 10 min, and centrifuged at 10,000 rpm at 4° C. for 15 min. After the supernatant was transferred into a sterile screw-top glass bottle, 0.5 ml of chloroform was added again and the lysate was stored at 4° C.

The recipient cell, L42-9 grown on No. 4 agar plate consisting of 0.5% glycerol, 0.5% yeast extract (Difco) and 0.5% MgSO$_4$.7H$_2$O was inoculated into a tube containing 5 ml of No. 4 medium and grown on a tube shaker at 30° C. overnight. One ml of the culture was transferred to 30 ml of the same medium in a 500-Erlenmyer flask and cultured at 30° C. for 3 hr. The culture was centrifuged for 15 min. The resulting pellet was suspended in 1.8 ml of 100 mM MC buffer consisting of 100 mM MgSO$_4$.7H$_2$O and 100 mM CaCl$_2$. 0.1 ml of the cell suspension was mixed with 0.1 ml of phage solution diluted 10-fold with 10 mM MC buffer in the tube and placed at for 60 min. After 0.8 ml of No. 4 medium was added, the tube was incubated at room temperature for 2 hr. The infected cell suspension of the volume of 0.2 ml was then spread on agar plates of No. 4 medium containing 100 μg/ml of kanamycin, and incubated at 27° C. for 5 days.

(ii) Screening of L-sorbose Reductase-deficient Mutants by Product Assay

Strains with Tn5 (Km$^r$) grown on No. 4-Km agar plate at 27° C. for 4 days were suspended in 50 μl of 0.15M citrate-Na$_2$HPO$_4$ buffer (pH 8.0) solution containing 4% L-sorbose per well of a 96 wells-microtiter plate and incubated at 30° C. for 24 hr without shaking. D-Sorbitol converted from L-sorbose was analyzed by thin layer chromatography (TLC) using 1 μl of the sample. The TLC analysis was carried out by using TLC plate of Kieselgel 60 F$_{254}$, Merck; solvent of ethyl acetate/isopropyl alcohol/acetic acid/H$_2$O=10:6:3.5:3; and spray reagents of 0.5% KIO4 solution and a tetrabase reagent prepared by mixing 2N-acetate saturated with tetrabase and 15% MnSO$_4$.4–6 H$_2$O (1:1 by volume).

By the TLC analysis, one mutant designated 26–9A was obtained as a candidate of L-sorbose reductase-deficient mutant. Strain 26–9A produced a faint amount of D-sorbitol from L-sorbose, while the other Tn5-mutants and the parent L42–9 produced significant amount of D-sorbitol.

(iii) Determination of L-sorbose Reductase Activity

Cells grown on 8% sorbitol-No. 5 medium consisting of 8% D-sorbitol, 1.5% yeast extract (Oriental Yeast Co., Osaka, Japan), 0.25% MgSO$_4$.7H$_2$O, 0.05% glycerol and 1.5% CaCO$_3$ (production grade) at 30° C. for 2 days were harvested by centrifugation and washed with 0.3% NaCl solution twice. The cell paste was suspended in 10 mM KH$_2$PO$_4$—K$_2$HPO$_4$ buffer (pH 7.0), and passed through a French pressure cell press twice. After centrifugation to remove intact cells, the supernatant was centrifuged at 100,000×g for 60 min. The resulting supernatant was collected as a source of L-sorbose reductase.

L-Sorbose reductase activity was determined by photometric assay in the presence of NADPH (T. Sugisawa et al., Agric. Biol. Chem., 55: 2043–2049, 1991). The reaction mixture contained 5 mg/ml of L-sorbose, 0.4 mg/ml of NADPH in 50 mM KH$_2$PO$_4$—K$_2$HPO$_4$ buffer (pH7.0) and 10 μl of enzyme solution. The change in absorption resulting from substrate-dependent oxidation of NADPH was followed at 340 nm with a Kontron spectrophotometer UVIKON 810. One unit of the reductase activity was defined as the amount of the enzyme catalyzing the formation of 1 μmole of NADP per min.

L-Sorbose reductase activities of strain 26-9A and its parent L42-9 were determined as described above to be less than 0.01 and 0.21 units/mg protein, respectively.

(iv) Colony Hybridization

Introduction of Tn5 fragment to the chromosome of the Strain 26-9A was confirmed by a colony blot hybridization with $^{32}$P-labeled Col E1::Tn5 DNA as the probe.

EXAMPLE 2

Cloning and Nucleotide Sequencing of Tn5-inserted Region

New Tn5-mutants were re-constructed by using pSUP202 (Ap$^r$Cm$^r$Tc$^r$; SimonR. et al., RIO/TECHNOL., 1: 784–791, 1983) with the DNA fragment containing Tn5 to confirm that L-sorbose reductase deficiency of 26-9A was caused by the Tn5 insertion, not by a mutation that may have simultaneously occurred in a different position of 26-9A DNA from the position of the Tn5 insertion. Southern-blot hybridization of various DNA fragments of strain 26-9A chromosome revealed that 13 kb EcoRV fragment containing a whole Tn5 had enough length (more than at least 1 kb) of DNA at both sides of the Tn5 insertion point for a double-crossing over recombination. The Eco RV fragment was cloned in pSUP202 to produce pSR02, which. was then introduced into G. melanogenus IFO 3293 to give Km$^r$Cm$^s$ strains, 3293EV-1 and 3293EV-9. Southern-blot hybridization analysis of the strains 3293EV-1 and 3293EV-9 revealed that both strains contained Tn5 without pSUP202 vector portion as strain 26-9A did (data not shown), indicating that homologous recombination by a double cross-over occurred. Deficiency of L-sorbose reductase activity in the strains 3293EV-1 and 3293EV-9 was examined by a product assay and a photometric enzyme assay as performed for strain 26-9A; new Tn5 mutants also produced undetectable L-sorbose-and showed L-sorbose reductase activity below 0.01 unit/mg cytosol protein, while G. melanogenus IFO 3293 showed L-sorbose reductase activity of 0.20 units/mg cytosol protein. It was concluded that the Tn5 insertion in 26-9A caused L-sorbose reductase deficiency.

The nucleotide sequence of Tn5-inserted region on pSR02 was determined by the dideoxy chain termination method (Sanger F. et al., Proc. Natl. Acad. Sci. USA., 74: 5463–5467, 1977) (FIG. 1). Analysis of the Tn5-inserted region by the homology search with BLASTP program (Lipman D. J. et al., J. Mol. Biol. 215: 403–410, 1990) revealed that the region encodes a polypeptide having a homology with polypeptides belonging to mannitol dehydrogenase (MDH) family. One of the member, mannitol 2-dehydrogenase (EC 1.1.1.67) of *Rhodobacter sphaeroides* (Schneider K.-H. et al, J. Gen. Microbiol., 1993) catalyzes the AND-dependent oxidation of mannitol into fructose. L-Sorbose reductase of Gluconobacter catalyzes not only the reduction of L-sorbose and D-fructose to produce D-sorbitol and D-mannitol in the presence of NADPH but also the oxidation of D-sorbitol and D-mannitol to produce L-sorbose and D-fructose in the presence of NADP (Sugisawa T. et al., ibid). The homology analysis indicated that polypeptide encoded by Tn5-disrupted gene of strain 26-9A is L-sorbose reductase gene itself, not its regulatory gene.

EXAMPLE 3

PCR Cloning

Partial L-sorbose reductase gene of G. suboxydans IFO 3291 was cloned by PCR amplification with a set of primers synthesized according to the amino acid sequences (SEQ ID NO: 3 and SEQ ID NO: 4) shown in FIG. 2; the degenerate primers were synthesized in consideration of the codon usage of Gluconobacter. The PCR gave about 300 bp product. Through Southern- and colony-hybridization analyses using this PCR-amplified fragment as a probe, complete L-sorbose reductase gene of G. suboxydans IFO 3291 was obtained in an 8.0 kb EcoRV fragment.

EXAMPLE 4

Determination of Nucleotide Sequence of L-sorbose Reductase Gene from G. suboxydans IFO 3291

Figure 3:
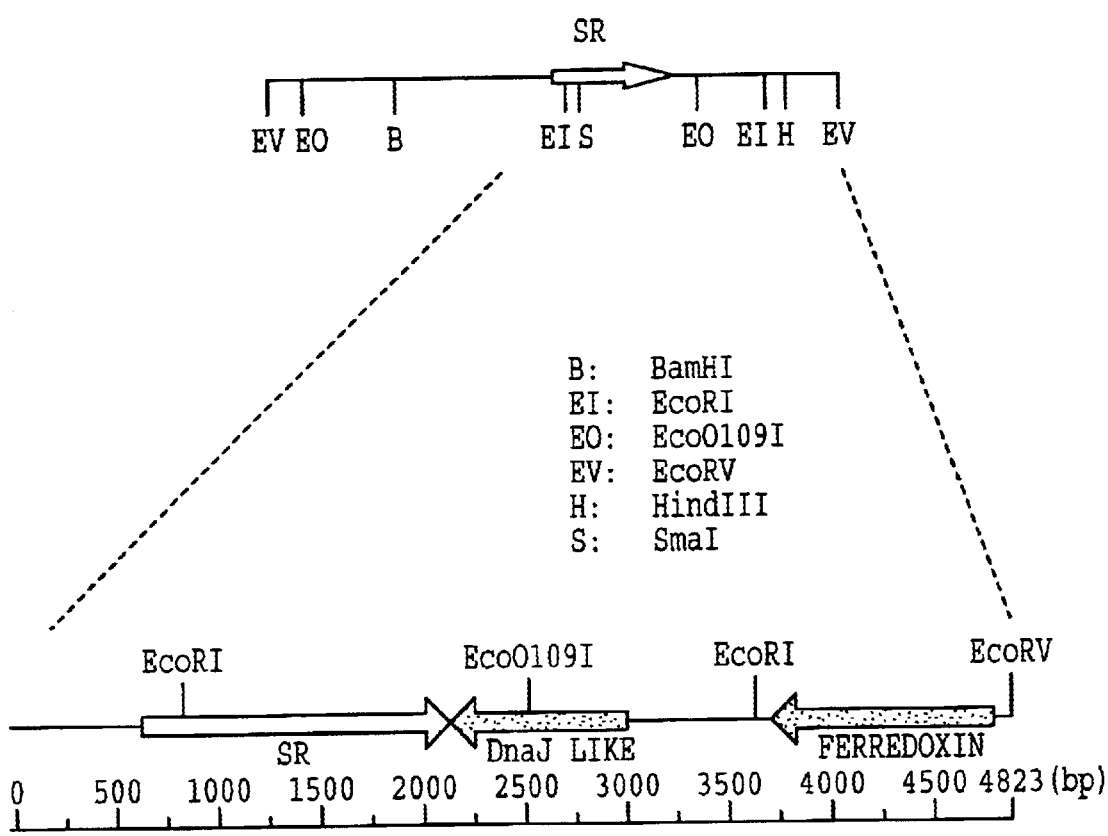
FIG. 3 illustrates Restriction map of 8.0 kb EcoRV fragment carrying L-sorbose reductase gene of *G. suboxydans* IFO 3291 (upper) and its enlarged region near the L-sorbose reductase gene (lower) showing ORFs found.

Complete nucleotide sequence of the L-sorbose reductase gene was determined with 8.0 kb of Eco RV fragment containing the L-sorbose reductase gene of G. suboxydans IFO 3291. The nucleotide sequence and deduced amino acid sequence are shown in SEQ ID NO: 1 and SEQ ID NO: 2. The restriction map of the 8.0 kb Eco RV is shown in FIG. 3. SR gene and two open reading frames which were found to be downstream of the L-sorbose reductase gene and encode polypeptides having homologies with DnaJ-like protein and ferredoxin, are located in the opposite direction. Upstream of the L-sorbose reductase gene, no relevant ORFs which possibly make an operon with the L-sorbose reductase gene were found. Therefore, disruption of the L-sorbose reductase gene was considered not to affect the expression of its neighboring genes.

EXAMPLE 5

Construction of L-sorbose Reductase Gene Disruptant from G. suboxydans IFO 3291

As can be taken from FIG. 4, the plasmid pUC4K, pSR03-1, and pSUP202 are the starting material plasmids. pUC4K is a source of Km resistant gene cassette and is available from Pharmacia (Uppsala, Sweden; Code No. 27-4958-01). The plasmid pSR03-1 is a derivative of the commercially available vector, pBluescript II SK (Stratagene CA, USA; Catalog No. 212205 and 212206) carrying EcoRV fragment obtained in Example 3. The vector pSUP202 is a derivative of pBR325 carrying a fragment containing a mob site, and as it is well known, pBR 325 is a derivative of pBR 322. Although pBR 325 itself does not seem to be commercially available, an alternative material, e.g. pBR 322 (ATCC 31344), pACYC177 (ATCC 37031) or pACYC184 (ATCC 37033) is believed to be readily applicable for the person skilled in the art, as described as pSUPseries by Simon R. et al. (1983, Bio/Technology 1: 784–791). Construction of a mob site-containing plasmid is also reported by Simon R. et al. (ibid).

FIG. 4 shows the scheme for the construction of a L-sorbose reductase gene targeting vector, pSUP202-SR::Km. Eco RV fragment of 8.0 kb was cloned in the Eco RI site of pBluescript II SK vector (Alting-Mees M. A. et al., Methods in enzymology 216: 483–95, Academic Press, London, 1992) to produce pSR03-1. A kanamycin-resistant-gene cassette (Km cassette) was inserted into an Eco RI site in the cloned L-sorbose reductase gene to obtain pSR04-1. This L-sorbose reductase gene disrupted with Km cassette was subcloned in a suicide vector pSUP202. The resulting pSR05-2, pSUP202-SR::Km (Km$^r$), was then introduced into G. suboxydans IFO3291 to obtain L-sorbose reductase-null mutant (Km$^r$). The aimed gene disruption was finally confirmed by Southern-hybridization analysis. A schematic mechanism for the disruption is illustrated in FIG. 5. A L-sorbose reductase deficient mutant SR3 was thus obtained.

L-sorbose reductase-gene-targeted mutant, SR3, and G. suboxydans IFO 3291 showed L-sorbose reductase activity of below 0.02 and 0.681 units/mg protein, respectively.

EXAMPLE 6

Fermentation Profile of Strain SR3 in 8% Sorbitol-No. 5 Medium

Figure 6A:
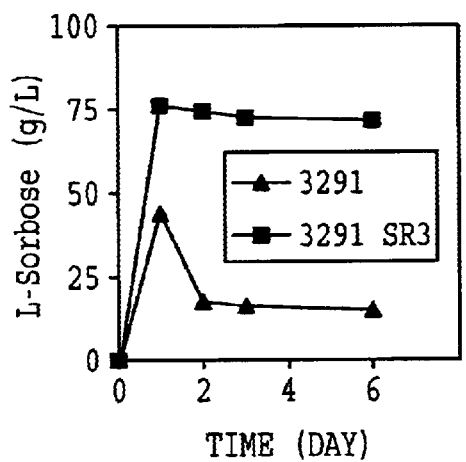
FIGS. 6(A–B) shows the graphs illustrating the fermentation profiles of strain SR3 and *G. suboxydans* IFO 3291 in 8% sorbitol-No. 5 medium.
Figure 6B:
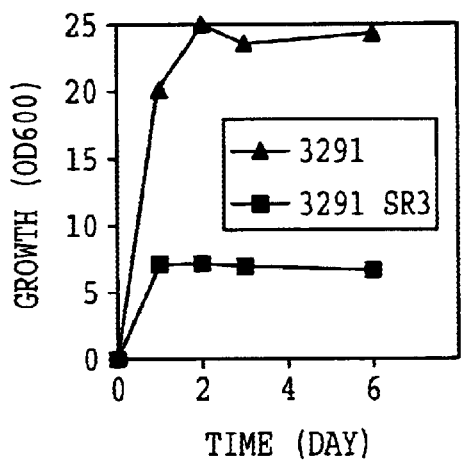

Growth and L-sorbose-assimilation profiles of strain SR3 and G. suboxydans IFO 3291 were evaluated with 8% sorbitol-No.5 medium in 500 ml Erlenmeyer flask (FIG. 6). Strain SR3 and G. suboxydans IFO 3291 could convert 80 g/L D-sorbitol to L-sorbose within 24 hr (data not shown).

*G. suboxydans* IFO3291 assimilated most of the converted L-sorbose within 48 hr. On the other hand, strain SR3 hardly utilized L-sorbose until the 3rd day; the remaining L-sorbose was more than 70 g/L. Strain SR3 and *G. suboxydans* IFO 3291 showed OD600 (cell growth) of 6.4 and 24 after 6 days, respectively.

EXAMPLE 7

Fermentation Profile of Strain SR3 in 2% Sorbitol-SCM Medium

Figure 7A:
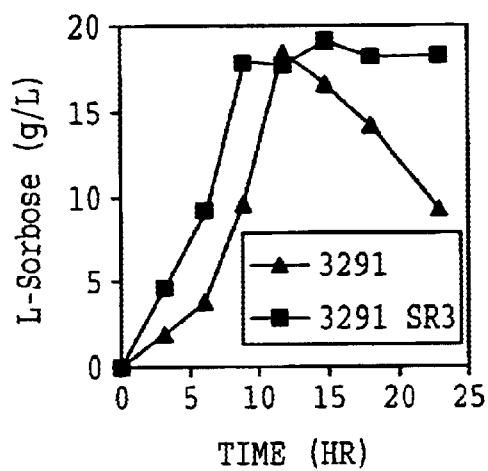
FIGS. 7(A–B) shows the graphs illustrating the fermentation profiles of strain SR3 and *G. suboxydans* IFO 3291 in 2% sorbitol-SCM medium.
Figure 7B:
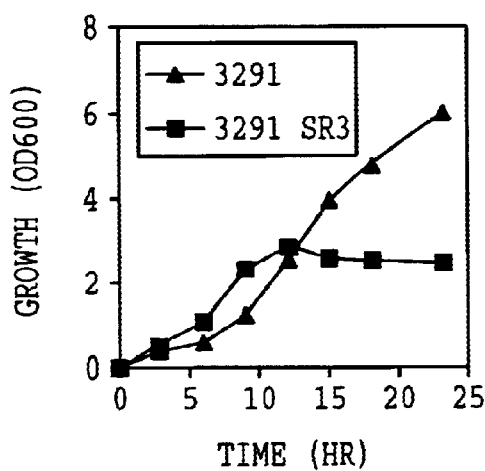

Growth and L-sorbose-assimilation profiles of strain SR3 and *G. suboxydans* IFO 3291 were evaluated with 2% sorbitol-SCM medium in 500 ml Erlenmeyer flask (FIG. 7). Strain SR3 and *G. suboxydans* IFO 3291 could convert 20 g/L D-sorbitol to L-sorbose within 12 hr. *G. suboxydans* IFO3291 assimilated half of the converted L-sorbose in 23 hr. On the other hand, strain SR3 hardly utilized L-sorbose. Strain SR3 and *G. suboxydans* IFO 3291 showed OD600 (cell growth) of 2.5 and 5.9 after 23 hr, respectively.

---

What is claimed is:

1. A genetically engineered microorganism obtained from a microorganism belonging to the genus Gluconobacter, said engineered microorganism comprising a mutated polynucleotide having a mutation in a polynucleotide selected from the group consisting of SEQ ID NO:1, a fragment of SEQ ID NO:1 encoding a polypeptide having L-sorbose reductase activity and a polynucleotide encoding SEQ ID NO:2, wherein the mutation results in a biological activity for reducing L-sorbose which is less than 10% of the amount of the activity of the non-mutated Gluconobacter microorganism.

2. A genetically engineered microorganism according to claim 1 wherein the polynucleotide consists of SEQ ID NO: 1.

3. A genetically engineered microorganism according to claim 1 wherein the mutation is located within a region required for formation of active L-sorbose reductase.

4. A genetically engineered microorganism according to claim 3 wherein the mutation results from the insertion of at least one interfering DNA fragment selected from the group consisting of transposons and antibiotic resistance gene cassettes.

5. A genetically engineered microorganism according to claim 3 wherein the mutation results from site directed mutagenesis.

6. A genetically engineered microorganism according to claim 3 wherein the region required for formation of active L-sorbose reductase lies in a DNA sequence selected from the group consisting of an encoding portion of an L-sorbose reductase gene and an expression control sequence therefor.

7. A genetically engineered microorganism according to claim 1, obtained from a microorganism which is selected from the group consisting of *Gluconobacter suboxydans* IFO 3291 and *Gluconobacter melanogenus* IFO 3293.

8. A method for producing L-sorbose which comprises:
   (a) incubating the genetically engineered microorganism according to claims 2 or 1 in a medium containing D-sorbitol or a source of D-sorbitol, and
   (b) obtaining L-sorbose from the medium.

9. A process for producing a genetically engineered microorganism of claim 1 comprising a) providing a Gluconobacter microorganism comprising a polypeptide selected from SEQ ID NO:1 or a fragment thereof encoding a polypeptide having L-sorbose reductase activity and b) introducing a mutation in said polynucleotide to result in a biological activity for reducing L-sorbose which is less than 10% of the amount of the activity of the non-mutated Gluconobacter microorganism.

10. A process for producing a genetically engineered microorganism comprising:
   a) providing a Gluconobacter microorganism comprising a polynucleotide selected from SEQ ID NO:1 or a fragment thereof encoding a polypeptide having L-sorbose reductase activity;
   (b) disrupting the polynucleotide by introducing a mutation into the polynucleotide;
   (c) determining the L-sorbose reductase activity of a microorganism comprising a mutated polynucleotide obtained in step (b);
   (d) selecting a microorganism based on step (c) in which L-sorbose reductase activity is less than 10% of the activity of the non-mutated Gluconobacter microorganism; and (e) introducing the mutated polynucleotide from the microorganism selected in step (d) into a microorganism of the genus Gluconobacterto produce a genetically engineered microorganism.

11. A method for producing a genetically engineered microorganism according to claim 10 wherein the polynucleotide consists of SEQ ID NO: 1.

* * * * *

SEQUENCE LISTING

<160> NUMBER OF SEQ ID NOS: 9

<210> SEQ ID NO 1
<211> LENGTH: 1458
<212> TYPE: DNA
<213> ORGANISM: Gluconobacter suboxydans

<400> SEQUENCE: 1

```
atgatcacgc acgaaaccct caagtctctt cccgccggtg tgcaggctcc gccctatgac    60
atcaatggga tcaaaccggg gatcgtgcat tttggcgtgg gaaacttctt ccgggcccat   120
gaggctttct acgttgaaca gatcctcaag gacgatccga actggggaat catcggcgtt   180
ggtctgacgg gtagcgacag gtcaaagaag aaggccgagg aattcaagaa gcaggactgc   240
ctcttttccc tgaccgaaac ggctccgtcc ggcaagagca cggttcgtgt tatgggcgcg   300
ctgagggatt accttttggc tcctgccgat ccggaagccg tgctgaagca tctcgctgac   360
ccgggaatcc gtatcgtttc catgacaatc acggaaggcg gttacaacat taacgagacg   420
acaggtgagt tcgatcttga gaacaaggcg gttcagcagg atctgaagac acccgaaacg   480
ccgtccacaa tctttggata tgttgtggaa ggactgcgcc gccgccgtga cgcaggtggc   540
aaggccttca cgatcatgtc ctgcgataat ctgcggcata acggtaatgt cgcccgcaag   600
gcatttctgg gatacgcgaa ggcccgtgat ccggaactgg ccaagtggat tgaagagaac   660
gcgacgttcc caaatggcat ggttgatcgc atcacgccga ccgtttctgc tgacattgcg   720
aagaagctca acgaagccag tggcctgcac gacgacctgc cgctcgttgc agaagacttt   780
catcagtggg tgctggaaga cagctttgct gatggccggc ctgcgctgga aaaggccgga   840
gtgcagttcg ttggggatgt gacggactac gagcatgtaa aaatccgcat gctgaatgct   900
ggtcacatca tgctctgctt cccggctgtt ctggcaggat ttgaaaatgt cgatcatgcc   960
cttgctgatc ccgatctacg gcgtatcctc gagaacttcc tgaacaaaga cgtcatcccg  1020
accctgaagg caccgccggg catgacgctg gaaggctatc gggacagcgt gatcagccgt  1080
ttctcgaatc cggccatggc ggatcagaca ttgcgtattt ccggggacgg gagctcgaag  1140
atccaggtct tctggacgga aacggtccgc aaggcttttg agggcaagcg cgatctgtcc  1200
cgcattgctt ttggtatggc atcctacctg gaaatgctgc gcggtaagga tgaaacgggt  1260
ggcacctacg agccattcga gccgactttt ggtgacaacc ataagactct ggccaaggct  1320
gatgattttg agagcgcgct caagctgcca gcgttcgatg cctggcgcga tctgagacg   1380
tccgggctga acaacaaggt tgtggagctt cgcaagatta tccgcgagaa gggcgtcaag  1440
gctgcccttc cggcctga                                                 1458
```

<210> SEQ ID NO 2
<211> LENGTH: 485
<212> TYPE: PRT
<213> ORGANISM: Gluconobacter suboxydans

<400> SEQUENCE: 2

```
Met Ile Thr His Glu Thr Leu Lys Ser Leu Pro Ala Gly Val Gln Ala
1               5                   10                  15

Pro Pro Tyr Asp Ile Asn Gly Ile Lys Pro Gly Ile Val His Phe Gly
            20                  25                  30

Val Gly Asn Phe Phe Arg Ala His Glu Ala Phe Tyr Val Glu Gln Ile
            35                  40                  45

Leu Lys Asp Asp Pro Asn Trp Gly Ile Ile Gly Val Gly Leu Thr Gly
    50                  55                  60

Ser Asp Arg Ser Lys Lys Lys Ala Glu Glu Phe Lys Lys Gln Asp Cys
65                  70                  75                  80

Leu Phe Ser Leu Thr Glu Thr Ala Pro Ser Gly Lys Ser Thr Val Arg
                85                  90                  95

Val Met Gly Ala Leu Arg Asp Tyr Leu Leu Ala Pro Ala Asp Pro Glu
            100                 105                 110

Ala Val Leu Lys His Leu Ala Asp Pro Gly Ile Arg Ile Val Ser Met
            115                 120                 125

Thr Ile Thr Glu Gly Gly Tyr Asn Ile Asn Glu Thr Thr Gly Glu Phe
130                 135                 140

Asp Leu Glu Asn Lys Ala Val Gln Gln Asp Leu Lys Thr Pro Glu Thr
145                 150                 155                 160

Pro Ser Thr Ile Phe Gly Tyr Val Val Glu Gly Leu Arg Arg Arg Arg
                165                 170                 175

Asp Ala Gly Gly Lys Ala Phe Thr Ile Met Ser Cys Asp Asn Leu Arg
            180                 185                 190

His Asn Gly Asn Val Ala Arg Lys Ala Phe Leu Gly Tyr Ala Lys Ala
            195                 200                 205

Arg Asp Pro Glu Leu Ala Lys Trp Ile Glu Glu Asn Ala Thr Phe Pro
    210                 215                 220

Asn Gly Met Val Asp Arg Ile Thr Pro Thr Val Ser Ala Asp Ile Ala
225                 230                 235                 240

Lys Lys Leu Asn Glu Ala Ser Gly Leu His Asp Asp Leu Pro Leu Val
                245                 250                 255

Ala Glu Asp Phe His Gln Trp Val Leu Glu Asp Ser Phe Ala Asp Gly
            260                 265                 270

Arg Pro Ala Leu Glu Lys Ala Gly Val Gln Phe Val Gly Asp Val Thr
            275                 280                 285

Asp Tyr Glu His Val Lys Ile Arg Met Leu Asn Ala Gly His Ile Met
    290                 295                 300

Leu Cys Phe Pro Ala Val Leu Ala Gly Phe Glu Asn Val Asp His Ala
305                 310                 315                 320

Leu Ala Asp Pro Asp Leu Arg Arg Ile Leu Glu Asn Phe Leu Asn Lys
                325                 330                 335

Asp Val Ile Pro Thr Leu Lys Ala Pro Pro Gly Met Thr Leu Glu Gly
            340                 345                 350

Tyr Arg Asp Ser Val Ile Ser Arg Phe Ser Asn Pro Ala Met Ala Asp
            355                 360                 365

Gln Thr Leu Arg Ile Ser Gly Asp Gly Ser Ser Lys Ile Gln Val Phe
```

-continued

```
                370                 375                 380
Trp Thr Glu Thr Val Arg Lys Ala Phe Glu Gly Lys Arg Asp Leu Ser
385                 390                 395                 400

Arg Ile Ala Phe Gly Met Ala Ser Tyr Leu Glu Met Leu Arg Gly Lys
                405                 410                 415

Asp Glu Thr Gly Gly Thr Tyr Glu Pro Phe Glu Pro Thr Phe Gly Asp
            420                 425                 430

Asn His Lys Thr Leu Ala Lys Ala Asp Asp Phe Glu Ser Ala Leu Lys
            435                 440                 445

Leu Pro Ala Phe Asp Ala Trp Arg Asp Leu Glu Thr Ser Gly Leu Asn
        450                 455                 460

Asn Lys Val Val Glu Leu Arg Lys Ile Ile Arg Glu Lys Gly Val Lys
465                 470                 475                 480

Ala Ala Leu Pro Ala
                485

<210> SEQ ID NO 3
<211> LENGTH: 8
<212> TYPE: PRT
<213> ORGANISM: Gluconobacter suboxydans

<400> SEQUENCE: 3

Met Thr Ile Thr Glu Gly Gly Tyr
1               5

<210> SEQ ID NO 4
<211> LENGTH: 8
<212> TYPE: PRT
<213> ORGANISM: Gluconobacter suboxydans

<400> SEQUENCE: 4

Phe Pro Asn Gly Met Val Asp Arg
1               5

<210> SEQ ID NO 5
<211> LENGTH: 90
<212> TYPE: DNA
<213> ORGANISM: Gluconobacter suboxydans

<400> SEQUENCE: 5
tacgagaacg tggatgacgc gatcgaggac aaggatctgc ggggcaacct tgagaactac      60
ctgaacaagg acgtcatccc gaccctgaag                                      90

<210> SEQ ID NO 6
<211> LENGTH: 90
<212> TYPE: DNA
<213> ORGANISM: Gluconobacter suboxydans
<220> FEATURE:
<221> NAME/KEY: misc_feature
<222> LOCATION: (1)..(90)
<223> OTHER INFORMATION: v can be a or c or g; n can be a or g or c or
      t; w can be a or t; y can be c or t

<400> SEQUENCE: 6
vvvctgaagg caccgccgng cwtgacgytt gagggttatc gggacagcgt catcagccgc      60
ttttcgaaca aggccatgtc tgatcagacg                                      90

<210> SEQ ID NO 7
<211> LENGTH: 23
<212> TYPE: DNA
<213> ORGANISM: Gluconobacter suboxydans
```

-continued

```
<220> FEATURE:
<221> NAME/KEY: misc_feature
<222> LOCATION: (1)..(23)
<223> OTHER INFORMATION: s can be c or g; y can be c or t; r can be a or
      g; h can be a or c or t.

<400> SEQUENCE: 7
atgacsatya csgargghgg hta                                             23

<210> SEQ ID NO 8
<211> LENGTH: 23
<212> TYPE: DNA
<213> ORGANISM: Gluconobacter suboxydans
<220> FEATURE:
<221> NAME/KEY: misc_feature
<222> LOCATION: (1)..(23)
<223> OTHER INFORMATION: b can be c or g or t; y can be c or t; h can be
      a or c or t.

<400> SEQUENCE: 8
ttcccbaayg ghatggtbga ycg                                             23

<210> SEQ ID NO 9
<211> LENGTH: 23
<212> TYPE: DNA
<213> ORGANISM: Gluconobacter suboxydans
<220> FEATURE:
<221> NAME/KEY: misc_feature
<222> LOCATION: (1)..(23)
<223> OTHER INFORMATION: r can be a or g; v can be a or c or g; d can be
      a or g or t.

<400> SEQUENCE: 9
cgrtcvacca tdccrttvgg gaa                                             23
```